US012674805B2

(12) United States Patent
McEwan et al.

(10) Patent No.: US 12,674,805 B2
(45) Date of Patent: Jul. 7, 2026

(54) COMPLIANCE METHOD

(71) Applicant: Nicoventures Trading Limited, London (GB)

(72) Inventors: Michael McEwan, London (GB); George Grant Hardie, London (GB); Oscar Camacho, London (GB)

(73) Assignee: NICOVENTURES TRADING LIMITED, London (GB)

( * ) Notice: Subject to any disclaimer, the term of this patent is extended or adjusted under 35 U.S.C. 154(b) by 942 days.

(21) Appl. No.: 17/638,746

(22) PCT Filed: Aug. 28, 2020

(86) PCT No.: PCT/GB2020/052066
§ 371 (c)(1),
(2) Date: Feb. 25, 2022

(87) PCT Pub. No.: WO2021/038239
PCT Pub. Date: Mar. 4, 2021

(65) Prior Publication Data

US 2022/0299529 A1 Sep. 22, 2022

(30) Foreign Application Priority Data

Aug. 30, 2019 (GB) ..................................... 1912520

(51) Int. Cl.
*G01N 33/68* (2006.01)

(52) U.S. Cl.
CPC ... *G01N 33/6893* (2013.01); *G01N 2800/307* (2013.01); *G01N 2800/52* (2013.01)

(58) Field of Classification Search
CPC ......... G01N 33/6893; G01N 2800/307; G01N 2800/52
See application file for complete search history.

(56) References Cited

U.S. PATENT DOCUMENTS

2013/0316926 A1 11/2013 Caffrey
2019/0221297 A1 7/2019 Satake

FOREIGN PATENT DOCUMENTS

JP 2018181352 A 11/2018

OTHER PUBLICATIONS

Bergmark E., "Hemoglobin Adducts of Acrylamide and Acrylonitrile in Laboratory Workers, Smokers and Nonsmokers," Chemical Research in Toxicology, American Chemical Society, Washington DC, US, Jan. 20, 1997, vol. 10, No. 1, XP009155884, ISSN: 0893-228X, DOI: 10.1021/TX960113P, pp. 78-84.

Fennell T.R., et al., "Hemoglobin Adducts from Acrylonitrile and Ethylene Oxide in Cigarette Smokers: Effects of Glutathione S-Transferase T1-Null and M1-Null Genotypes," Cancer Epidemiology, Biomarkers & Prevention, Jul. 2000, vol. 9, pp. 705-712.

International Search Report and Written Opinion for Application No. PCT/GB2020/052066, mailed Nov. 30, 2020, 15 pages.

Newland N., et al., "Evaluating the Effects of Switching from Cigarette Smoking to using a Heated Tobacco Product on Health Effect Indicators in Healthy Subjects: Study Protocol for a Randomized Controlled Trial," Internal and Emergency Medicine, Springer Milan, May 2, 2019, vol. 14, No. 6, XP036876998, ISSN: 1828-0447, DOI: 10.1007/S11739-019-02090-8, [retrieved on May 2, 2019], pp. 885-898.

Perez H.L., et al., "Adducts of Acrylonitrile with Hemoglobin in Nonsmokers and in Participants in a Smoking Cessation Program," Chemical Research in Toxicology, Oct. 1, 1999, vol. 12, No. 10, XP055736771, ISSN: 0893-228X, DOI: 10.1021/tx9900728, pp. 869-873.

Phillips D.H., "Smoking-Related DNA and Protein Adducts in Human Tissues," Carcinogenesis, Dec. 2002, vol. 23, No. 12, pp. 1979-2004.

Scherer G., et al.,"A Correlation Study Applied to Biomarkers of Internal and Effective Dose for Acrylonitrile and 4-Aminobiphenyl in Smokers," Biomarkers, Jun. 29, 2014, vol. 19, No. 4, XP055743403, ISSN: 1354-750X, DOI: 10.3109/1354750X.2014.910271, pp. 291-301.

Shepperd C.J., et al., "A Single-Blinded, Single-Centre, Controlled Study in Healthy Adult Smokers to Identify the Effects of a Reduced Toxicant Prototype Cigarette on Biomarkers of Exposure and of Biological Effect Versus Commercial Cigarettes," BMC Public Health, Biomed Central, London, GB, Jul. 29, 2013, vol. 13, No. 1, XP021159156, ISSN: 1471-2458, DOI: 10.1186/1471-2458-13-690, 16 pages.

Shepperd C.J., et al., "Changes in Levels of Biomarkers of Exposure and Biological Effect in a Controlled Study of Smokers Switched from Conventional Cigarettes to Reduced-Toxicant-Prototype Cigarettes," Regulatory Toxicology and Pharmacology, May 10, 2015, vol. 72, No. 2, XP055743366, ISSN: 0273-2300, DOI: 10.1016/j.yrtph.2015.04.016, pp. 273-291.

Forster M., Fiebelkorn S., Yurteri C., Mariner D., Liu C., Wright C., McAdam K.G., Murphy, J., Proctor C.J. 2018. Assessment of novel tobacco heating product THP1.0. Part 3: Comprehensive chemical characterisation of harmful and potentially harmful aerosol emissions. Regul Toxicol Pharmacol. 93:14-33.

Gale N., McEwan M., Eldrige A.C., Fearon Im. et al., (2018). A randomised, controlled, two-centre open-label study in healthy Japanese subjects to evaluate the effect on biomarkers of exposure of switching from a conventional cigarette to a tobacco heating product. BMC Public Health. 2017; 16: 637.

(Continued)

*Primary Examiner* — Lyle A Alexander
(74) *Attorney, Agent, or Firm* — Womble Bond Dickinson (US) LLP; Mark R. DeLuca

(57) ABSTRACT

The present disclosure relates to methods incorporating the use of a biomarker (CEVal) for assessing compliance with a smoking cessation program, for example, a smoking cessation program which involves subjects switching from conventional cigarettes to a hybrid device, an e-cigarette and/or a tobacco heating product, a smoking cessation program involving the use of nicotine replacement therapy, a smoking cessation program involving lifestyle choices or therapy, or a combination thereof.

10 Claims, No Drawings

(56) References Cited

OTHER PUBLICATIONS

McEwan, M., Gale, N., Ebajemito, J., Camacho, O.M., Murphy, J., Hardie, G., Proctor, C.J. (2019). A Comparison of Two Clinical Studies Investigating Changes in Exposure to Cigarette Smoke Chemicals in Smokers Who Switch to Using a Tobacco Heating Product for a Five Day Period. Poster presented at Society of Toxicology meeting in Baltimore Mar. 10 to 14, 2019.

Gregg, E.O., Minet, E., McEwan, M. (2013). Urinary biomarkers of smokers' exposure to tobacco smoke constituents in tobacco products assessment: a fit for purpose approach. Biomarkers 18(6):467-486.

Rogman A., Perfetti, T.A. (2013) The chemical components of tobacco and tobacco smoke. CRC Press, Taylor & Francis Inc (United States).

Margham, J., McAdam, K., Forster, M., Liu, C., Wright, C., Mariner, D., Proctor, C. Chemical Composition of Aerosol from an E-Cigarette: A Quantitative Comparison with Cigarette Smoke. Chem. Res. Toxicol. 2016 29, 10, 1662-1678.

COMPLIANCE METHOD

PRIORITY CLAIM

The present application is a National Phase entry of PCT Application No. PCT/GB2020/052066, filed Aug. 28, 2020, which claims priority from United Kingdom Application No. 1912520.2, filed Aug. 30, 2019, each of which is hereby fully incorporated herein by reference.

TECHNICAL FIELD

The present disclosure relates to the use of a biomarker for assessing compliance with a smoking cessation program, for example, a smoking cessation program which involves subjects switching from conventional cigarettes to a hybrid device, an e-cigarette and/or a tobacco heating product, a smoking cessation program involving the use of nicotine replacement therapy, a smoking cessation program involving lifestyle choices or therapy, or a combination thereof. Also described is a method for assessing compliance involving the biomarker.

BACKGROUND

The health risks associated with cigarette smoking are well-documented in the art, and whilst the optimum way to reduce or eliminate these risks is by complete cessation of smoking, smokers often find it difficult to stop smoking completely. Smoking cessation programs may therefore involve the use of non-combustible aerosol provision systems such as hybrid devices, e-cigarettes or tobacco heating products (THPs) used as cigarette replacements. Such systems are classed as Potentially Reduced Risk Products (PRRPs) since along with reductions in emissions of toxicants compared to combustible cigarettes, studies have been carried out demonstrating that PRRP use can lead to a reduction in the burden of toxicants taken into the body of the consumer. An accurate picture of how PRRP use can reduce smoking-related health risks is, however, only possible if subjects adhere to a smoking cessation program, and if such program is carried out with an ambulatory approach instead of a confined approach. An ambulatory approach has the benefits of allowing subjects to use these products in their natural environment, but results in difficulties around monitoring subjects' behavior and compliance.

There is therefore an ongoing need in the art for a method of assessing compliance with a smoking cessation program. For example, a program involving switching from cigarettes to PRRPs, nicotine replacement therapy and/or lifestyle choices or therapy, and applying an ambulatory approach without subject confinement.

SUMMARY

According to the first aspect of the present disclosure, there is provided the use of N-(2-cyanoethyl) valine (CEVal) as a biomarker for compliance with a smoking cessation program. In various embodiments of the first aspect, the level of N-(2-cyanoethyl) valine (CEVal) may be measured in a biological assay and said level compared with a reference CEVal level to stratify the subjects according to compliance with the smoking cessation program.

According to the second aspect of the present disclosure, there is provided a method of assessing compliance with a smoking cessation program, said method comprising:

(a) providing one or more blood samples from a subject;
(b) measuring the level of N-(2-cyanoethyl) valine (CEVal) from the one or more blood samples of the subject in a biological assay;
(c) comparing the level obtained in step (b) with reference levels of CEVal for the smoking cessation program; and
(d) stratifying the subject according to compliance with the smoking cessation program based on the comparison in step (c).

In various embodiments of the second aspect, steps (a), (b), (c) and (d) may be carried out repeatedly during the course of the smoking cessation program to assess the subject's continued compliance. The method may further comprise step (e), modifying or maintaining the smoking cessation program for the subject based on the stratification in step (d).

In various embodiments of both the first and second aspects, the smoking cessation program may comprise lifestyle choices, therapy, or a combination thereof. Such lifestyle choices may involve changes to diet and/or exercise, and therapy may comprise drug therapy and/or psychological counselling. The smoking cessation program may further comprise nicotine replacement therapy as discussed herein and/or use of a non-combustible aerosol provision system.

In various embodiments of both the first and second aspects, the smoking cessation program may comprise switching from combustible smoking articles to a non-combustible aerosol provision system, e.g. switching from cigarettes to a hybrid device, an e-cigarette, a tobacco heating product or a combination thereof. The smoking cessation program may further comprise nicotine replacement therapy and/or lifestyle choices, therapy or a combination thereof.

In various embodiments of both the first and second aspects, the smoking cessation program may comprise nicotine replacement therapy. Such therapy is discussed in more detail below. The smoking cessation program may further comprise lifestyle choices, therapy or a combination thereof, and/or use of a non-combustible aerosol provision system.

The smoking cessation program may have a length of greater than 5 days, particularly at least about 80 days and preferably between about 90 days and about 360 days. The skilled person will appreciate, however, that the length of the smoking cessation program is not restrictive and the present disclosure is not limited to a specific program length.

The reference CEVal level may be indicative of compliance or non-compliance with the smoking cessation program, or may be indicative of compliance, partial compliance or non-compliance with the smoking cessation program. The terms "compliance", "partial compliance" and "non-compliance" are defined herein.

In various embodiments of both the first and second aspects, the reference CEVal levels at about day 80 to about day 100 of the smoking cessation program are:

i. <about 78 to <about 40 pmol/g Hb CEVal for compliance; and
ii. ≥about 60 to ≥about 78 pmol/g Hb CEVal for non-compliance;

provided that (i) and (ii) are different.

In various embodiments of both the first and second aspects, the reference CEVal levels at about day 80 to about day 100 of the smoking cessation program are:

i. <about 78 to <about 40 pmol/g Hb CEVal for compliance;
ii. between about 60 and about 164 pmol/g Hb CEVal for partial compliance; and
iii. >about 78 to >about 164 pmol/g Hb CEVal for non-compliance;

provided that (i), (ii) and (iii) are different.

In various embodiments of both the first and second aspects, the reference CEVal levels at about day 80 to about day 100 of the smoking cessation program are:

i. <about 78 to <about 40 pmol/g Hb CEVal for compliance;
ii. between about 60 and about 150 pmol/g Hb CEVal for partial compliance; and
iii. >about 78 to >about 150 pmol/g Hb CEVal for non-compliance;

provided that (i), (ii) and (iii) are different.

In various embodiments of both the first and second aspects the reference CEVal levels at about day 80 to about day 100 of the smoking cessation program are:

i. <about 76 pmol/g Hb CEVal for compliance;
ii. between about 76 and about 142 pmol/g Hb CEVal for partial compliance; and
iii. >about 142 pmol/g Hb CEVal for non-compliance;

provided that (i), (ii) and (iii) are different.

In various embodiments of the present disclosure, the reference CEVal levels at about day 170 to about day 190 of the smoking cessation program are:

i. <about 54 to <about 35 pmol/g Hb CEVal for compliance; and
ii. ≥about 35 to ≥54 pmol/g Hb CEVal for non-compliance;

provided that (i) and (ii) are different.

or i. <about 54 to <about 35 pmol/g Hb CEVal for compliance;
ii. between about 35 and about 112 pmol/g Hb CEVal for partial compliance; and
iii. >about 60 to >about 112 pmol/g Hb CEVal for non-compliance;

provided that (i), (ii) and (iii) are different.

In various embodiments of the present disclosure, the reference CEVal levels at about day 170 to about day 190 of the smoking cessation program are:

i. <about 45 to <about 25 pmol/g Hb CEVal for compliance;
ii. between about 25 and about 100 pmol/g Hb CEVal for partial compliance; and
iii. >about 45 to >about 100 pmol/g Hb CEVal for non-compliance;

provided that (i), (ii) and (iii) are different.

In various embodiments of the present disclosure, the reference CEVal levels at about day 170 to about day 190 of the smoking cessation program are:

i. <about 25 pmol/g Hb CEVal for compliance;
ii. between about 25 and about 77 pmol/g Hb CEVal for partial compliance; and
iii. >about 77 pmol/g Hb CEVal for non-compliance;

provided that (i), (ii) and (iii) are different.

In various embodiments of the present disclosure, the reference CEVal levels at about day 350 to about day 370 are:

i. <about 35 to <about 20 pmol/g Hb CEVal for compliance; and
ii. ≥about 20 to ≥about 35 pmol/g Hb CEVal for non-compliance;

provided that (i) and (ii) are different.

or i. <about 35 to <about 20 pmol/g Hb CEVal for compliance;
ii. between about 20 and about 78 pmol/g Hb CEVal for partial compliance; and
iii. >about 40 to >about 78 pmol/g Hb CEVal for non-compliance;

provided that (i), (ii) and (iii) are different.

In various embodiments of the present disclosure, the reference CEVal levels at about day 350 to about day 370 are:

i. <about 25 to <about 10 pmol/g Hb CEVal for compliance;
ii. between about 10 and about 40 pmol/g Hb CEVal for partial compliance; and
iii. >about 20 pmol/g Hb CEVal for non-compliance;

provided that (i), (ii) and (iii) are different.

In various embodiments of the present disclosure, the reference CEVal levels at about day 350 to about day 370 are:

i. <about 10 pmol/g Hb CEVal for compliance;
ii. between about 10 and about 22 pmol/g Hb CEVal for partial compliance; and
iii. >about 22 pmol/g Hb CEVal for non-compliance;

provided that (i), (ii) and (iii) are different.

These embodiments are set out in the appended independent and dependent claims. It will be appreciated that features of the dependent claims may be combined with each other and with features of the independent claims in combinations other than those explicitly set out in the claims. Furthermore, the approaches described herein are not restricted to specific embodiments such as those set out below, but include and contemplate any appropriate combinations of features presented herein. For example, a use and/or method may be provided in accordance with approaches described herein which includes any one or more of the various features described below as appropriate.

DETAILED DESCRIPTION

Features of certain examples and embodiments are discussed and described herein. Some features of certain examples and embodiments may be implemented conventionally and these are not discussed or described in detail in the interests of brevity. It will thus be appreciated that features of apparatus, uses and methods discussed herein which are not described in detail may be implemented in accordance with any conventional techniques for implementing such features.

As used herein, the term “combustible smoking article” is intended to refer to cigarettes, cigarillos, cigars, and tobacco for pipes or roll-your-own/make-your-own cigarettes (whether based on tobacco, tobacco derivatives, expanded tobacco, or reconstituted tobacco). The combustible smoking article may be referred to herein as “a cigarette”, “a conventional cigarette”, “a cigarette product”, “a conventional cigarette product” and/or “a combustible cigarette”.

The term “non-combustible aerosol provision system” is intended to refer to heating devices that release compounds from aerosolizable materials without burning the aerosolizable material. These systems or devices include electronic cigarettes (e-cigarettes), tobacco heating products (THPs), and hybrid systems to generate aerosol using a combination of aerosolizable materials. In various embodiments of the present disclosure, the non-combustible aerosol provision system is an e-cigarette, a tobacco heating product, or a hybrid device. These systems or devices may be referred to as Potential Reduced Risk Products or PRRPs.

As is common in the art, the terms “vapor” and “aerosol” and related terms such as “vaporize”, “volatilize” and “aerosolize” may be used interchangeably. Aerosol provision systems or devices may therefore be referred to herein as "vapor provision systems or devices", "aerosol delivery systems or devices", "electronic vapor provision systems or devices", "electronic aerosol provision systems or devices", or "e-cigarettes or electronic cigarettes".

The present disclosure provides the use of N-(2-cyanoethyl) valine (CEVal) as a biomarker for compliance with a smoking cessation program, and a method for assessing compliance with a smoking cessation program involving the biomarker N-(2-cyanoethyl) valine. These aspects of the present disclosure are surprisingly able to provide an accurate and reliable indication of a subject's compliance with a smoking cessation program involving e.g. PRRPs, nicotine replacement therapy, lifestyle choices, therapy or a combination thereof. CEVal has been found to be both specific and sensitive to exposure to smoke from conventional cigarette products as opposed to exposure to smoke and/or nicotine from use of PRRPs or nicotine replacements.

In arriving at the present disclosure, the inventors recognized that long-term studies were required to assess potential reductions in smoking-related health risks from e.g. PRRPs but that such studies presented difficulties in monitoring subject compliance because they required an ambulatory approach rather than a confined approach. Confinement allows direct involvement and control of subject compliance, whereas long-term ambulatory studies allow subjects to use products in their natural environment without such involvement and control.

Notably, without direct involvement and control, a substantial number of subjects give inaccurate information to the smoking cessation program provider about their smoking habits. This information can include (1) whether a subject has actually complied and quit smoking conventional cigarettes in favor of PRRPs, nicotine replacement and/or lifestyle choices or therapy; (2) whether a subject has not complied at all with smoking cessation; and (3) whether a subject is partially complying by "cutting down" smoking of conventional cigarettes alongside use of the PRRP, nicotine replacement, lifestyle choices and/or therapy.

Accurate information on a subject's actual cessation status and compliance—particularly around sole use of PRRP, dual use of PRRP and cigarettes, and complete non-compliance with switching to the PRRP—is, however, critical to understanding if the subjects are in compliance, and thereby derive whether there are any health benefits of using e.g. PRRPs instead of cigarettes.

One of the approaches for monitoring subjects' compliance is to use one or more biomarkers. Biomarkers are molecules whose measurement provides information as to the state of a subject. To be successful for compliance with a smoking cessation program, such biomarkers need to therefore be specific for exposure to smoke from conventional cigarette products as opposed to e.g. vapor from PRRPs, as well as have the sensitivity to detect whether a subject is smoking conventional cigarettes as well as using, e.g. the PRRP. The present inventors surprisingly found that N-(2-cyanoethyl) valine or CEVal meets these requirements.

N-(2-cyanoethyl) valine or CEVal is a hemoglobin adduct which is formed through exposure to acrylonitrile. Acrylonitrile interacts with hemoglobin at the N-terminal valine according to the following addition mechanism:

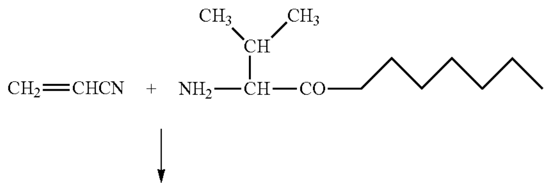

-continued

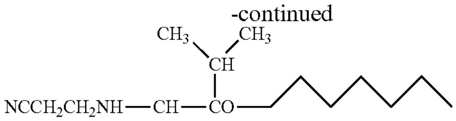

Although exposure to acrylonitrile can occur in the environment, the main source of exposure aside from cigarette smoke is occupational. Acrylonitrile is primarily used in industry, where it is used to make other chemicals such as plastics, synthetic rubber and acrylic fibers. Generally in non-smokers the level of CEVal is therefore low. In various studies, non-smokers have been reported to have CEVal levels below the limit of detection, whereas smokers have been reported to have much higher levels.

The high levels of CEVal arise because acrylonitrile is produced at temperatures ranging from 500 to 800° C. These levels are not, however, seen with non-combustible aerosol provision devices such as hybrid devices, e-cigarettes and tobacco heating products, or with nicotine replacement, lifestyle choices or therapy. Accordingly, the present inventors were advantageously able to develop a method for assessing compliance of a subject with a smoking cessation program through the use of CEVal as a biomarker. In particular, the present inventors were able to use CEVal as a biomarker for compliance with a smoking cessation program involving use of a non-combustible aerosol provision device, nicotine replacement therapy and/or lifestyle choices, therapy or a combination thereof.

The specificity and sensitivity of CEVal surprisingly enables subjects to be stratified into groups based on compliance vs non-compliance, as well as compliance, partial compliance and non-compliance, thereby identifying subjects undertaking in dual use of conventional cigarettes with the non-combustible aerosol provision device.

For ease of reference, these and further features of the present disclosure are now discussed under appropriate section headings. However, the teachings under each section are not necessarily limited to the section in which they are found.

Smoking Cessation Program

The present disclosure is centered on compliance with a smoking cessation program. The details of the smoking cessation program are not, however, particularly limited and may be any cessation program known or developed by the skilled person according to normal practice in the art.

In various embodiments of the present disclosure, the smoking cessation program involves a subject stopping their use of combustible smoking articles. It may involve a replacement smoking product such as a non-combustible aerosol provision system and/or nicotine replacement therapy, or it may not. The smoking cessation program may instead involve other means to mitigate the physical and/or psychological withdrawal symptoms which are known in the art to make smoking cessation difficult. For example, the smoking cessation program may comprise a behavior modification program involving non-nicotine drug therapy, psychological counselling and/or lifestyle choices. Such lifestyle choices may involve changes in diet, changes in exercise or a combination thereof.

Consequently, in various embodiments of the present disclosure, the smoking cessation program involves lifestyle choices, therapy or a combination thereof. For example, the smoking cessation program may involve psychological counselling alongside changes in diet, changes in exercise or a combination thereof. The smoking cessation program may further comprise nicotine replacement therapy as described herein, use of a non-combustible aerosol provision system, or a combination of nicotine replacement therapy and a non-combustible aerosol provision system.

In various embodiments of the present disclosure, the smoking cessation program comprises switching from combustible smoking articles to a non-combustible aerosol provision system. The terms "combustible smoking article" and "non-combustible aerosol provision system" are defined above. The combustible smoking article is most likely to be cigarettes. The non-combustible aerosol provision system is typically a hybrid product, an e-cigarette, a tobacco heating product or a combination thereof. The smoking cessation program may further comprise nicotine replacement therapy as described herein, lifestyle choices, therapy or a combination thereof.

In various embodiments of the present disclosure, the smoking cessation program comprises switching from combustible smoking articles to nicotine replacement therapy. Examples of nicotine replacement therapy may include gums, lozenges, and transdermal nicotine-delivery patches or the like. The smoking cessation program may further comprise lifestyle choices, therapy or a combination thereof, where lifestyle choices and therapy are as defined herein, e.g. psychological counselling in combination with nicotine replacement therapy. The smoking cessation program may further comprise use of a non-combustible aerosol provision system, e.g. nicotine replacement therapy in combination with an e-cigarette, a tobacco heating product or a hybrid device, optionally with lifestyle choices, therapy or a combination thereof.

The term "switching" has its normal meaning in the art. Namely to substitute or exchange one item for another. In the context of this disclosure, the smoking cessation program may involve a subject exchanging or switching their use of combustible smoking articles (e.g. cigarettes) for a non-combustible aerosol provision system, nicotine replacement therapy, lifestyle choices, therapy or a combination thereof. The exchange, substitution or switch is absolute in the sense that the intention of the program is for the subject to only use the replacement system, therapy, choices etc.

The length of the smoking cessation program is not limited; as the skilled person would readily understand, the present disclosure is not concerned with a particular program length, only the compliance of a subject to the program being followed. As mentioned above, the smoking cessation program may adopt an ambulatory approach.

In various embodiments of the present disclosure, the smoking cessation program is not a confined program. In various embodiments, the smoking cessation program is an ambulatory program.

With an ambulatory approach, the smoking cessation program can run for an extended period of time, for example, the smoking cessation program may have a length of greater than 5 days. In various embodiments of the present disclosure, the smoking cessation program has a length of at least about 80 days, e.g., between about 90 days and about 360 days.

N-(2-cyanoethyl) valine as a biomarker

N-(2-cyanoethyl valine), otherwise known as CEVal, is formed by acrylonitrile interacting with the N-terminal amino group of hemoglobin. Red blood cells have a relatively long-life time of around 90 to 120 days, meaning that hemoglobin adducts are particularly useful as markers of exposure. They can provide information over an extended period of time. Hemoglobin is also available from blood in large amounts, which is an important practical advantage when compared with the analysis of e.g., DNA adducts or the like.

Biomarkers can be generally measured and detected through a variety of assays, methods and detection systems known to the person skilled in the art. The term "measuring", "detecting" or "taking a measurement" refers in the context of this disclosure to a quantitative determination of the level of CEVal in a subject's blood sample. The level may be determined by one observation under a set of conditions, or an average (e.g., mean) of a plurality of observations under the same set of conditions. In various embodiments of the present disclosure, the level of CEVal is determined with one observation or single analysis point.

Methods for measuring biomarkers, include but are not limited to, refractive index spectroscopy, ultra-violet spectroscopy, fluorescence analysis, radio-chemical analysis, near-infrared spectroscopy, infrared spectroscopy, nuclear magnetic resonance spectroscopy, light scattering analysis, mass spectrometry, pyrolysis mass spectroscopy, nephelometry, dispersive Raman spectroscopy, gas chromatography, liquid chromatography, gas chromatography combined with mass spectrometry, liquid chromatography combined with mass spectrometry, matrix-assisted laser desorption ionization-time of flight combined with mass spectrometry, ion spray spectroscopy combined with mass spectrometry, capillary electrophoresis, colorimetry and surface plasmon resonance.

In the present disclosure, any of the above methods may be used and the skilled person is readily able to determine which method would be most appropriate. In various embodiments, however, the level of CEVal is determined with gas chromatography combined with mass spectrometry (GC-MS) as described in Scherer, G., Newland, K., Papadopoulou, E., Minet, E., *A correlation study applied to biomarkers of internal and effective dose for acrylonitrile and 4-Aminobiphenyl in smokers, Biomarkers,* 2014 June; 19(4):291-301.

CEVal is a modified amino acid formed by acrylonitrile interacting with the N-terminal amino group of hemoglobin. This biomarker may therefore be detected either as a protein or amino acid. As will be appreciated by the skilled person, protein assays may be done using standard techniques such as ELISA assays. Also, the amino acid form of the biomarker can be measured in an appropriate assay In various embodiments of the present disclosure, the level of CEVal is measured in a biological assay and said level is compared with a reference CEVal level. The reference CEVal levels are pre-determined levels, measured according to the GC-MS method described above, that are associated with a level of subject compliance at various time intervals after T0 (T0 being the start of the smoking cessation program).

In various embodiments of the present disclosure, the level of CEVal is therefore measured in a biological assay and said level is compared with a reference CEVal level to stratify subjects according to compliance with the smoking cessation program. The reference CEVal level allows a relationship to be determined between the measured CEVal level and subject compliance. This is highly advantageous for the purposes of long-term studies with a smoking cessation program, e.g., a program involving PRRPs, nicotine replacement therapy, lifestyle choices, therapy or a combination thereof, as a replacement for conventional cigarettes.

In various embodiments of the present disclosure, the reference CEVal level is indicative of compliance or non-compliance with the smoking program. In this instance, the term "compliance" means that the subject is either solely or mainly using the non-combustible aerosol provision system. For example, the subject has completely replaced their use of combustible smoking articles (e.g. cigarettes or the like) with a replacement product or technique (e.g. a non-combustible aerosol provision system such as an e-cigarette, hybrid device, tobacco heating product or a combination thereof, nicotine replacement therapy, lifestyle choices, therapy or a combination thereof), or has substantially replaced their use of combustible smoking articles with a replacement product or technique.

The terms "mainly" or "substantially" are used herein to recognize that a subject may be compliant with a smoking cessation program involving replacement of combustible smoking articles with e.g., non-combustible aerosol provision systems, nicotine replacement therapy, lifestyle choices, therapy or a combination thereof, but have a temporal relapse. The phrases "mainly compliant" or "substantially compliant" can thus be understood to mean use of up to about 4 cigarettes a week or less than about 4 cigarettes a week.

Non-compliance is used herein to mean that the subject has either not or not completely replaced their use of combustible smoking articles (e.g., cigarettes or the like). The subject may have, for instance, only partially replaced their use of combustible smoking articles with e.g., a non-combustible aerosol provision system, nicotine replacement therapy, lifestyle choices, therapy or a combination thereof.

The terms "partially" or "not completely" are used herein to recognize subjects who are not wholly compliant with the smoking cessation program, and who have more than a temporal relapse to smoking cigarettes. The phrases "partially compliant" or "not completely compliant" can thus be understood to mean use of greater than about 4 cigarettes a week.

The reference CEVal levels are measured/established at various time intervals from T0. This is because CEVal is a hemoglobin adduct and thereby dependent on the lifecycle of red blood cells in a subject; the CEVal level will therefore change depending on the time that has passed from the beginning of the smoking cessation program and the time at which the sample is obtained and tested.

In various embodiments of the present disclosure, at about day 80 to about day 100 of the smoking cessation program, i.e. at about day 80 to about 100 from T0 (e.g. about day 90), the reference level of CEVal may be:

i. less than (<) about 78 to less than (<) about 40 pmol/g Hb CEVal for compliance; and
ii. equal to or greater than (≥) about 60 to equal to or greater than (≥) about 78 pmol/g Hb CEVal for non-compliance;
provided that (i) and (ii) are different.

Compliant subjects having a CEVal level of less than about 78 to less than about 40 pmol/g Hb may smoke up to about 4 cigarettes a week, whereas non-compliant subjects having a CEVal level of ≥about 60 to ≥about 78 pmol/g Hb may smoke more than about 4 cigarettes a week. The skilled person will understand that there is no overlap between compliance and non-compliance and that the avoidance of overlap is the purpose of the proviso.

In various embodiments of the present disclosure, the reference CEVal levels at about day 80 to about day 100 (e.g. about day 90) of the smoking cessation program are:

i. <78 pmol/g Hb CEVal for compliance; and
ii. ≥65 to ≥78 pmol/g Hb CEVal for non-compliance;
provided that (i) and (ii) are different.

In various embodiments of the present disclosure, the reference CEVal levels at about day 80 to about day 100 (e.g. about day 90) of the smoking cessation program are:

i. <78 pmol/g Hb CEVal for compliance; and
ii. ≥70 to ≥78 pmol/g Hb CEVal for non-compliance;
provided that (i) and (ii) are different.

In various embodiments of the present disclosure, the reference CEVal levels at about day 80 to about day 100 (e.g. about day 90) of the smoking cessation program are:

i. <78 pmol/g Hb CEVal for compliance; and
ii. ≥75 to ≥78 pmol/g Hb CEVal for non-compliance;
provided that (i) and (ii) are different.

In various embodiments of the present disclosure, the reference CEVal levels at about day 80 to about day 100 (e.g. about day 90) of the smoking cessation program are:

i. <78 pmol/g Hb CEVal for compliance; and
ii. ≥78 pmol/g Hb CEVal for non-compliance.

In various embodiments of the present disclosure, the reference CEVal levels at about day 80 to about day 100 (e.g. about day 90) of the smoking cessation program are:

i. <76 pmol/g Hb CEVal for compliance; and
ii. ≥76 pmol/g Hb CEVal for non-compliance.

In various embodiments of the present disclosure, at about day 150 to about day 200 (e.g. about day 170 to day 190) of the smoking cessation program, i.e. day 150 to day 200 or day 170 to day 190 from T0, the reference CEVal levels are:

i. <about 54 to <about 35 pmol/g Hb CEVal for compliance; and
ii. ≥about 35 to ≥about 54 pmol/g Hb CEVal for non-compliance;
provided that (i) and (ii) are different.

In various embodiments of the present disclosure, the reference CEVal levels at about day 150 to about day 200 (e.g. about day 170 to about day 190) of the smoking cessation program are:

i. <about 54 to <about 40 pmol/g Hb CEVal for compliance; and
ii. ≥about 35 to ≥about 54 pmol/g Hb CEVal for non-compliance;
provided that (i) and (ii) are different.

In various embodiments of the present disclosure, the reference CEVal levels at about day 150 to about day 200 (e.g. about day 170 to about day 190) of the smoking cessation program are:

i. <about 54 to <about 45 pmol/g Hb CEVal for compliance; and
ii. ≥about 35 to ≥about 54 pmol/g Hb CEVal for non-compliance;
provided that (i) and (ii) are different.

In various embodiments of the present disclosure, the reference CEVal levels at about day 150 to about day 200 (e.g. about day 170 to about day 190) of the smoking cessation program are:

i. <about 54 to <about 50 pmol/g Hb CEVal for compliance; and
ii. ≥about 35 to ≥about 54 pmol/g Hb CEVal for non-compliance;
provided that (i) and (ii) are different.

In various embodiments of the present disclosure, the reference CEVal levels at about day 150 to about day 200 (e.g. about day 170 to about day 190) of the smoking cessation program are:

i. <about 54 to pmol/g Hb CEVal for compliance; and
ii. ≥about 35 to ≥about 54 pmol/g Hb CEVal for non-compliance
provided that (i) and (ii) are different. ;

In various embodiments of the present disclosure, at about day 150 to about day 200 (e.g. about day 170 to day 190) of the smoking cessation program, i.e. day 150 to day 200 or day 170 to day 190 from T0, the reference CEVal levels are:

i. <about 54 to <about 35 pmol/g Hb CEVal for compliance; and
ii. ≥about 40 to ≥about 54 pmol/g Hb CEVal for non-compliance;
provided that (i) and (ii) are different.

In various embodiments of the present disclosure, at about day 150 to about day 200 (e.g. about day 170 to day 190) of the smoking cessation program, i.e. day 150 to day 200 or day 170 to day 190 from T0, the reference CEVal levels are:

i. <about 54 to <about 35 pmol/g Hb CEVal for compliance; and
ii. ≥about 45 to ≥about 54 pmol/g Hb CEVal for non-compliance;
provided that (i) and (ii) are different.

In various embodiments of the present disclosure, at about day 150 to about day 200 (e.g. about day 170 to day 190) of the smoking cessation program, i.e. day 150 to day 200 or day 170 to day 190 from T0, the reference CEVal levels are:

i. <about 54 to <about 35 pmol/g Hb CEVal for compliance; and
ii. ≥about 50 to ≥about 54 pmol/g Hb CEVal for non-compliance;
provided that (i) and (ii) are different.

In various embodiments of the present disclosure, at about day 150 to about day 200 (e.g. about day 170 to day 190) of the smoking cessation program, i.e. day 150 to day 200 or day 170 to day 190 from T0, the reference CEVal levels are:

i. <about 54 to <about 40 pmol/g Hb CEVal for compliance; and
ii. ≥about 40 to ≥about 54 pmol/g Hb CEVal for non-compliance;
provided that (i) and (ii) are different.

In various embodiments of the present disclosure, at about day 150 to about day 200 (e.g. about day 170 to day 190) of the smoking cessation program, i.e. day 150 to day 200 or day 170 to day 190 from T0, the reference CEVal levels are:

i. <about 54 to <about 45 pmol/g Hb CEVal for compliance; and
ii. ≥about 45 to ≥about 54 pmol/g Hb CEVal for non-compliance;
provided that (i) and (ii) are different.

In various embodiments of the present disclosure, at about day 150 to about day 200 (e.g. about day 170 to day 190) of the smoking cessation program, i.e. day 150 to day 200 or day 170 to day 190 from T0, the reference CEVal levels are:

i. <about 54 to <about 50 pmol/g Hb CEVal for compliance; and
ii. ≥about 50 to ≥about 54 pmol/g Hb CEVal for non-compliance;
provided that (i) and (ii) are different.

In various embodiments of the present disclosure, at about day 150 to about day 200 (e.g. about day 170 to day 190) of the smoking cessation program, i.e. day 150 to day 200 or day 170 to day 190 from T0, the reference CEVal levels are:

i. <about 54 pmol/g Hb CEVal for compliance; and
ii. ≥about 54 pmol/g Hb CEVal for non-compliance;
provided that (i) and (ii) are different.

In various embodiments of the present disclosure, at about day 150 to about day 200 (e.g. about day 170 to day 190) of the smoking cessation program, i.e. day 150 to day 200 or day 170 to day 190 from T0, the reference CEVal levels are:

i. <about 54 to <about 20 pmol/g Hb CEVal for compliance; and
ii. ≥about 20 to ≥about 54 pmol/g Hb CEVal for non-compliance;
provided that (i) and (ii) are different.

In various embodiments of the present disclosure, at about day 150 to about day 200 (e.g. about day 170 to day 190) of the smoking cessation program, i.e. day 150 to day 200 or day 170 to day 190 from T0, the reference CEVal levels are:

i. <about 54 to <about 25 pmol/g Hb CEVal for compliance; and
ii. ≥about 25 to ≥about 54 pmol/g Hb CEVal for non-compliance;
provided that (i) and (ii) are different.

In various embodiments of the present disclosure, at about day 150 to about day 200 (e.g. about day 170 to day 190) of the smoking cessation program, i.e. day 150 to day 200 or day 170 to day 190 from T0, the reference CEVal levels are:

i. <about 54 to <about 20 pmol/g Hb CEVal for compliance; and
ii. ≥about 20 to ≥about 54 pmol/g Hb CEVal for non-compliance;
provided that (i) and (ii) are different.

In various embodiments of the present disclosure, at about day 150 to about day 200 (e.g. about day 170 to day 190) of the smoking cessation program, i.e. day 150 to day 200 or day 170 to day 190 from T0, the reference CEVal levels are:

i. <about 30 to <about 25 pmol/g Hb CEVal for compliance; and
ii. ≥about 25 to ≥about 30 pmol/g Hb CEVal for non-compliance;
provided that (i) and (ii) are different.

In various embodiments of the present disclosure, at about day 150 to about day 200 (e.g. about day 170 to day 190) of the smoking cessation program, i.e. day 150 to day 200 or day 170 to day 190 from T0, the reference CEVal levels are:

i. <about 25 pmol/g Hb CEVal for compliance; and
ii. ≥about 25 pmol/g Hb CEVal for non-compliance;
provided that (i) and (ii) are different.

In each of the above embodiments of the present disclosure, the terms compliance and non-compliance are as defined above.

In various embodiments of the present disclosure, at about day 300 to about day 370 of the smoking cessation program, (e.g. about day 350 to about day 370) i.e. day 300 to day 370 from T0 or day 350 to day 370 from T0, the reference CEVal levels are:

i. <about 35 to <about 20 pmol/g Hb CEVal for compliance; and
ii. ≥about 20 to ≥about 35 pmol/g Hb CEVal for non-compliance;
provided that (i) and (ii) are different.

In various embodiments of the present disclosure, the reference CEVal levels at about day 300 to about day 370 (e.g. about day 350 to about day 370) are:

i. <about 35 to <about 25 pmol/g Hb CEVal for compliance; and
ii. ≥about 20 to ≥about 35 pmol/g Hb CEVal for non-compliance;
provided that (i) and (ii) are different.

In various embodiments of the present disclosure, at about day 300 to about day 370 of the smoking cessation program, (e.g. about day 350 to about day 370) i.e. day 300 to day 370 from T0 or day 350 to day 370 from T0, the reference CEVal levels are:

i. <about 35 to <about 30 pmol/g Hb CEVal for compliance; and ii. ≥about 20 to ≥about 35 pmol/g Hb CEVal for non-compliance;

provided that (i) and (ii) are different.

In various embodiments of the present disclosure, at about day 300 to about day 370 of the smoking cessation program, (e.g. about day 350 to about day 370) i.e. day 300 to day 370 from T0 or day 350 to day 370 from T0, the reference CEVal levels are:

i. <about 35 pmol/g Hb CEVal for compliance; and ii. ≥about 20 to ≥about 35 pmol/g Hb CEVal for non-compliance;

provided that (i) and (ii) are different.

In various embodiments of the present disclosure, at about day 300 to about day 370 of the smoking cessation program, (e.g. about day 350 to about day 370) i.e. day 300 to day 370 from T0 or day 350 to day 370 from T0, the reference CEVal levels are:

i. <about 35 to <about 20 pmol/g Hb CEVal for compliance; and ii. ≥about 25 to ≥about 35 pmol/g Hb CEVal for non-compliance;

provided that (i) and (ii) are different.

In various embodiments of the present disclosure, at about day 300 to about day 370 of the smoking cessation program, (e.g. about day 350 to about day 370) i.e. day 300 to day 370 from T0 or day 350 to day 370 from T0, the reference CEVal levels are:

i. <about 35 to <about 20 pmol/g Hb CEVal for compliance; and ii. ≥about 30 to ≥about 35 pmol/g Hb CEVal for non-compliance;

provided that (i) and (ii) are different.

In various embodiments of the present disclosure, at about day 300 to about day 370 of the smoking cessation program, (e.g. about day 350 to about day 370) i.e. day 300 to day 370 from T0 or day 350 to day 370 from T0, the reference CEVal levels are:

i. <about 35 to <about 25 pmol/g Hb CEVal for compliance; and ii. ≥about 25 to ≥about 35 pmol/g Hb CEVal for non-compliance;

provided that (i) and (ii) are different.

In various embodiments of the present disclosure, at about day 300 to about day 370 of the smoking cessation program, (e.g. about day 350 to about day 370) i.e. day 300 to day 370 from T0 or day 350 to day 370 from T0, the reference CEVal levels are:

i. <about 35 to <about 30 pmol/g Hb CEVal for compliance; and ii. ≥about 30 to ≥about 35 pmol/g Hb CEVal for non-compliance;

provided that (i) and (ii) are different.

In various embodiments of the present disclosure, at about day 300 to about day 370 of the smoking cessation program, (e.g. about day 350 to about day 370) i.e. day 300 to day 370 from T0 or day 350 to day 370 from T0, the reference CEVal levels are:

i. <about 35 to pmol/g Hb CEVal for compliance; and ii. ≥about 35 pmol/g Hb CEVal for non-compliance;

provided that (i) and (ii) are different.

In various embodiments of the present disclosure, at about day 300 to about day 370 of the smoking cessation program, (e.g. about day 350 to about day 370) i.e. day 300 to day 370 from T0 or day 350 to day 370 from T0, the reference CEVal levels are:

i. <about 35 to <about 10 pmol/g Hb CEVal for compliance; and ii. ≥about 10 to ≥about 35 pmol/g Hb CEVal for non-compliance;

provided that (i) and (ii) are different.

In various embodiments of the present disclosure, at about day 300 to about day 370 of the smoking cessation program, (e.g. about day 350 to about day 370) i.e. day 300 to day 370 from T0 or day 350 to day 370 from T0, the reference CEVal levels are:

i. <about 25 to <about 10 pmol/g Hb CEVal for compliance; and ii. ≥about 10 to ≥about 25 pmol/g Hb CEVal for non-compliance;

provided that (i) and (ii) are different.

In various embodiments of the present disclosure, at about day 300 to about day 370 of the smoking cessation program, (e.g. about day 350 to about day 370) i.e. day 300 to day 370 from T0 or day 350 to day 370 from T0, the reference CEVal levels are:

i. <about 10 pmol/g Hb CEVal for compliance; and ii. ≥about 10 CEVal for non-compliance;

provided that (i) and (ii) are different.

In various embodiments of the present disclosure the CEVal reference levels (in pmol/g Hb) and time periods may be as follows:

| | Day 80 to Day 100 | Day 170 to Day 190 | Day 350 to Day 370 | Estimated cigarettes/week |
|---|---|---|---|---|
| Compliant | <78 to <40 | <54 to <35 | <35 to <20 | up to 4 |
| Non-compliant | ≥60 to ≥78 | ≥32 to ≥54 | ≥20 to ≥35 | >4 |

In an example embodiment of the present disclosure, the CEVal reference levels (in pmol/g Hb) and time periods may be:

| | Day 80 to Day 100 | Day 170 to Day 190 | Day 350 to Day 370 | Estimated cigarettes/week |
|---|---|---|---|---|
| Compliant | <78 | <54 | <35 | up to 4 |
| Non-compliant | ≥78 | ≥54 | ≥35 | >4 |

In other various embodiments of the present disclosure the CEVal reference levels (in pmol/g Hb) and time periods may be as follows:

| | Day 80 to Day 100 | Day 170 to Day 190 | Day 350 to Day 370 | Estimated cigarettes/week |
|---|---|---|---|---|
| Compliant | <78 to <40 | <54 to <20 | <35 to <10 | up to 4 |
| Non-compliant | ≥60 to ≥78 | ≥20 to ≥54 | ≥10 to ≥35 | >4 |

In an example embodiment of the present disclosure, the CEVal reference levels (in pmol/g Hb) and time periods may be:

| | Day 80 to Day 100 | Day 170 to Day 190 | Day 350 to Day 370 | Estimated cigarettes/week |
|---|---|---|---|---|
| Compliant | <76 | <25 | <10 | up to 4 |
| Non-compliant | ≥76 | ≥25 | ≥10 | >4 |

Other embodiments are equally described above.

The present disclosure may therefore involve CEVal being used as a biomarker at time point between day 80 to day 100, and again at a time point between day 300 to day 370 or between day 350 to day 370 in order to determine subject compliance at each of the time points with the smoking cessation program. This approach may, for example, be adopted where a subject is deemed to be compliant at the first time period.

In various embodiments of the present disclosure, CEVal may be used as a biomarker at a time point between day 80 to day 100, and again at a time point between day 150 to day 200 or between day 170 and day 190 in order to determine subject compliance at each of the time points with the smoking cessation program. This approach may, for example, be adopted where a subject is deemed to be non-compliant at the first time period. Further use of CEVal as a biomarker may then be carried out at a time point between day 350 to day 370 for a further assessment of compliance.

Decisions on the continuance of the smoking cessation program and/or modifications thereof may be made depending on whether a subject is classified as compliant or non-compliant. Such modifications are discussed in more detail below.

In various embodiments of the present disclosure, the reference CEVal level is indicative of compliance, partial compliance or non-compliance with the smoking program. In this instance, the term "compliance" has the same meaning as described above; with a smoking cessation program involving switching from a combustible smoking article to a non-combustible aerosol provision system, nicotine replacement therapy, lifestyle choices, therapy or a combination thereof, it can be quantified as use of up to about 4 cigarettes a week.

The term "partial compliance" means that the subject has only partially replaced their use of combustible smoking articles. "Partial compliance" may also be referred to "dual use". The subject is typically smoking combustible smoking articles along side the smoking cessation program. Partial compliance with a smoking cessation program involving a switch from or exchange of cigarettes for e.g. an e-cigarette, tobacco heating product, a hybrid device, nicotine replacement therapy, lifestyle choices, therapy or a combination thereof, may be quantified as use of greater than 4 to about 10 cigarettes per week.

Non-compliance may be quantified in this context as use of greater than about 10 cigarettes a week.

The skilled person will appreciate that there is no overlap between compliance, partial compliance and non-compliance. The groups are distinct from one another to enable accurate stratification of subjects to be conducted. Consequently, the ranges for the CEVal levels below are presented with the proviso that compliance, partial compliance and non-compliance represent different values.

In the same manner as described above, the reference CEVal levels may be measured/established at various time intervals from T0. Hence, in various embodiments of the present disclosure, at about day 80 to about day 100 of the smoking cessation program, i.e. at about day 80 to about 100 from T0 (e.g. about day 90), the reference level of CEVal may be:

i. <about 78 to <about 40 pmol/g Hb CEVal for compliance;
ii. between about 60 pmol/g Hb and about 164 pmol/g Hb CEVal for partial compliance; and
iii. >about 78 to >about 164 pmol/g Hb CEVal for non-compliance;
provided that (i), (ii) and (iii) are different.

Compliance, partial compliance (dual use) and non-compliance are defined above.

In various embodiments of the present disclosure, the reference CEVal levels at about day 80 to about day 100 of the smoking cessation program are:

i. <about 78 to <about 40 pmol/g Hb CEVal for compliance;
ii. between about 65 pmol/g Hb and about 164 pmol/g Hb CEVal for partial compliance; and
iii. >about 78 to >about 164 pmol/g Hb CEVal for non-compliance; provided that (i), (ii) and (iii) are different.

In various embodiments of the present disclosure, the reference CEVal levels at about day 80 to about day 100 of the smoking cessation program are:

i. <about 78 to <about 40 pmol/g Hb CEVal for compliance;
ii. between about 70 pmol/g Hb and about 164 pmol/g Hb CEVal for partial compliance; and
iii. >about 78 to >about 164 pmol/g Hb CEVal for non-compliance;
provided that (i), (ii) and (iii) are different.

In various embodiments of the present disclosure, the reference CEVal levels at about day 80 to about day 100 of the smoking cessation program are:

i. <about 78 to <about 40 pmol/g Hb CEVal for compliance;
ii. between about 75 pmol/g Hb and about 164 pmol/g Hb CEVal for partial compliance; and
iii. >about 78 to >about 164 pmol/g Hb CEVal for non-compliance;
provided that (i), (ii) and (iii) are different.

In various embodiments of the present disclosure, the reference CEVal levels at about day 80 to about day 100 of the smoking cessation program are:

i. <about 78 to <about 40 pmol/g Hb CEVal for compliance;
ii. between about 78 pmol/g Hb and about 164 pmol/g Hb CEVal for partial compliance; and
iii. >about 78 to >about 164 pmol/g Hb CEVal for non-compliance;
provided that (i), (ii) and (iii) are different.

In various embodiments of the present disclosure, the reference CEVal levels at about day 80 to about day 100 of the smoking cessation program are:

i. <about 78 to <about 40 pmol/g Hb CEVal for compliance;
ii. between about 60 pmol/g Hb and about 164 pmol/g Hb CEVal for partial compliance; and
iii. >about 80 to >about 164 pmol/g Hb CEVal for non-compliance;
provided that (i), (ii) and (iii) are different.

In various embodiments of the present disclosure, the reference CEVal levels at about day 80 to about day 100 of the smoking cessation program are:

i. <about 78 to <about 40 pmol/g Hb CEVal for compliance;
ii. between about 60 pmol/g Hb and about 164 pmol/g Hb CEVal for partial compliance; and
iii. >about 85 to >about 164 pmol/g Hb CEVal for non-compliance;
provided that (i), (ii) and (iii) are different.

In various embodiments of the present disclosure, the reference CEVal levels at about day 80 to about day 100 of the smoking cessation program are:

i. <about 78 to <about 40 pmol/g Hb CEVal for compliance;
ii. between about 60 pmol/g Hb and about 164 pmol/g Hb CEVal for partial compliance; and
iii. >about 90 to >about 164 pmol/g Hb CEVal for non-compliance;
provided that (i), (ii) and (iii) are different.

In various embodiments of the present disclosure, the reference CEVal levels at about day 80 to about day 100 of the smoking cessation program are:

i. <about 78 to <about 40 pmol/g Hb CEVal for compliance;
ii. between about 60 pmol/g Hb and about 164 pmol/g Hb CEVal for partial compliance; and
iii. >about 100 to >about 164 pmol/g Hb CEVal for non-compliance;
provided that (i), (ii) and (iii) are different.

In various embodiments of the present disclosure, the reference CEVal levels at about day 80 to about day 100 of the smoking cessation program are:

i. <about 78 to <about 40 pmol/g Hb CEVal for compliance;
ii. between about 60 pmol/g Hb and about 164 pmol/g Hb CEVal for partial compliance; and
iii. >about 120 to >about 164 pmol/g Hb CEVal for non-compliance;
provided that (i), (ii) and (iii) are different.

In various embodiments of the present disclosure, the reference CEVal levels at about day 80 to about day 100 of the smoking cessation program are:

i. <about 78 to <about 40 pmol/g Hb CEVal for compliance;
ii. between about 60 pmol/g Hb and about 164 pmol/g Hb CEVal for partial compliance; and
iii. >about 140 to >about 164 pmol/g Hb CEVal for non-compliance;
provided that (i), (ii) and (iii) are different.

In various embodiments of the present disclosure, the reference CEVal levels at about day 80 to about day 100 of the smoking cessation program are:

i. <about 78 to <about 40 pmol/g Hb CEVal for compliance;
ii. between about 60 pmol/g Hb and about 164 pmol/g Hb CEVal for partial compliance; and
iii. >about 164 pmol/g Hb CEVal for non-compliance;
provided that (i), (ii) and (iii) are different.

In various embodiments of the present disclosure, the reference CEVal levels at about day 80 to about day 100 of the smoking cessation program are:

i. <about 78 to <about 40 pmol/g Hb CEVal for compliance;
ii. between about 65 pmol/g Hb and about 164 pmol/g Hb CEVal for partial compliance; and
iii. >about 164 pmol/g Hb CEVal for non-compliance;
provided that (i), (ii) and (iii) are different.

In various embodiments of the present disclosure, the reference CEVal levels at about day 80 to about day 100 of the smoking cessation program are:

i. <about 78 to <about 40 pmol/g Hb CEVal for compliance;
ii. between about 70 pmol/g Hb and about 164 pmol/g Hb CEVal for partial compliance; and
iii. >about 164 pmol/g Hb CEVal for non-compliance;
provided that (i), (ii) and (iii) are different.

In various embodiments of the present disclosure, the reference CEVal levels at about day 80 to about day 100 of the smoking cessation program are:

i. <about 78 to <about 40 pmol/g Hb CEVal for compliance;
ii. between about 75 pmol/g Hb and about 164 pmol/g Hb CEVal for partial compliance; and
iii. >about 164 pmol/g Hb CEVal for non-compliance;
provided that (i), (ii) and (iii) are different.

In various embodiments of the present disclosure, the reference CEVal levels at about day 80 to about day 100 of the smoking cessation program are:

i. <about 78 to <about 40 pmol/g Hb CEVal for compliance;
ii. between about 78 pmol/g Hb and about 164 pmol/g Hb CEVal for partial compliance; and
iii. >about 164 pmol/g Hb CEVal for non-compliance;
provided that (i), (ii) and (iii) are different.

Compliant subjects having a CEVal level of less than about 78 or less than about 40 pmol/g Hb may smoke up to about 4 cigarettes a week, whereas partially compliant subjects having a CEVal level of between about 60-78 pmol/g Hb and about 164 pmol/g Hb may smoke between about 4 and about 10 cigarettes a week, and non-compliant subjects having a CEVal level of greater than about 78-164 pmol/g Hb may smoke more than about 10 cigarettes a week.

In various embodiments of the present disclosure, the reference CEVal levels at about day 80 to about day 100 of the smoking cessation program are:

i. <about 78 to <about 40 pmol/g Hb CEVal for compliance;
ii. between about 60 pmol/g Hb and about 150 pmol/g Hb CEVal for partial compliance; and
iii. >about 150 pmol/g Hb CEVal for non-compliance;
provided that (i), (ii) and (iii) are different.

In various embodiments of the present disclosure, the reference CEVal levels at about day 80 to about day 100 of the smoking cessation program are:

i. <about 78 to <about 70 pmol/g Hb CEVal for compliance;
ii. between about 70 pmol/g Hb and about 145 pmol/g Hb CEVal for partial compliance; and
iii. >about 145 pmol/g Hb CEVal for non-compliance;
provided that (i), (ii) and (iii) are different.

In various embodiments of the present disclosure, the reference CEVal levels at about day 80 to about day 100 of the smoking cessation program are:

i. <about 78 to <about 75 pmol/g Hb CEVal for compliance;
ii. between about 75 pmol/g Hb and about 145 pmol/g Hb CEVal for partial compliance; and
iii. >about 145 pmol/g Hb CEVal for non-compliance;
provided that (i), (ii) and (iii) are different.

In various embodiments of the present disclosure, the reference CEVal levels at about day 80 to about day 100 of the smoking cessation program are:

i. <about 78 to <about 76 pmol/g Hb CEVal for compliance;
ii. between about 76 pmol/g Hb and about 142 pmol/g Hb CEVal for partial compliance; and
iii. >about 142 pmol/g Hb CEVal for non-compliance;
provided that (i), (ii) and (iii) are different.

In various embodiments of the present disclosure, the reference CEVal levels at about day 80 to about day 100 of the smoking cessation program are:

i. <about 76 pmol/g Hb CEVal for compliance;
ii. between about 76 pmol/g Hb and about 142 pmol/g Hb CEVal for partial compliance; and
iii. >about 142 pmol/g Hb CEVal for non-compliance;
provided that (i), (ii) and (iii) are different.

Compliant subjects having a CEVal level of less than about 78 or less than about 40 pmol/g Hb may smoke up to about 4 cigarettes a week, whereas partially compliant subjects having a CEVal level of between about 60-78 pmol/g Hb and about 150 pmol/g Hb may smoke between about 4 and about 10 cigarettes a week, and non-compliant subjects having a CEVal level of greater than about 142 pmol/g Hb may smoke more than about 10 cigarettes a week.

In various embodiments of the present disclosure, at about day 150 to about day 200 of the smoking cessation program (e.g. day 170 to day 190), i.e. day 150 to day 200 or day 170 to day 190 from T0, the reference CEVal levels are:

i. <about 54 to <about 35 pmol/g Hb CEVal for compliance;

ii. between about 35 and about 112 pmol/g Hb CEVal for partial compliance; and iii. >about 60 to >about 112 pmol/g Hb CEVal for non-compliance;

provided that (i), (ii) and (iii) are different.

In various embodiments of the present disclosure, the reference CEVal levels at about day 150 to about day 200 of the smoking cessation program (e.g. day 170 to day 190) are:

i. <about 54 to <about 35 pmol/g Hb CEVal for compliance;

ii. between about 40 and about 112 pmol/g Hb CEVal for partial compliance; and iii. >about 60 to >about 112 pmol/g Hb CEVal for non-compliance;

provided that (i), (ii) and (iii) are different.

In various embodiments of the present disclosure, the reference CEVal levels at about day 150 to about day 200 of the smoking cessation program (e.g. day 170 to day 190) are:

i. <about 54 to <about 35 pmol/g Hb CEVal for compliance;

ii. between about 45 and about 112 pmol/g Hb CEVal for partial compliance; and iii. >about 60 to >about 112 pmol/g Hb CEVal for non-compliance;

provided that (i), (ii) and (iii) are different.

In various embodiments of the present disclosure, the reference CEVal levels at about day 150 to about day 200 of the smoking cessation program (e.g. day 170 to day 190) are:

i. <about 54 to <about 35 pmol/g Hb CEVal for compliance;

ii. between about 50 and about 112 pmol/g Hb CEVal for partial compliance; and iii. >about 60 to >about 112 pmol/g Hb CEVal for non-compliance;

provided that (i), (ii) and (iii) are different.

In various embodiments of the present disclosure, the reference CEVal levels at about day 150 to about day 200 of the smoking cessation program (e.g. day 170 to day 190) are:

i. <about 54 to <about 35 pmol/g Hb CEVal for compliance;

ii. between about 60 and about 112 pmol/g Hb CEVal for partial compliance; and iii. >about 60 to >about 112 pmol/g Hb CEVal for non-compliance;

provided that (i), (ii) and (iii) are different.

In various embodiments of the present disclosure, the reference CEVal levels at about day 150 to about day 200 of the smoking cessation program (e.g. day 170 to day 190) are:

i. <about 54 to <about 35 pmol/g Hb CEVal for compliance;

ii. between about 54 and about 112 pmol/g Hb CEVal for partial compliance; and iii. >about 60 to >about 112 pmol/g Hb CEVal for non-compliance;

provided that (i), (ii) and (iii) are different.

In various embodiments of the present disclosure, the reference CEVal levels at about day 150 to about day 200 of the smoking cessation program (e.g. day 170 to day 190) are:

i. <about 54 to <about 35 pmol/g Hb CEVal for compliance;

ii. between about 35 and about 112 pmol/g Hb CEVal for partial compliance; and iii. >about 70 to >about 112 pmol/g Hb CEVal for non-compliance;

provided that (i), (ii) and (iii) are different.

In various embodiments of the present disclosure, the reference CEVal levels at about day 150 to about day 200 of the smoking cessation program (e.g. day 170 to day 190) are:

i. <about 54 to <about 35 pmol/g Hb CEVal for compliance;

ii. between about 35 and about 112 pmol/g Hb CEVal for partial compliance; and iii. >about 80 to >about 112 pmol/g Hb CEVal for non-compliance;

provided that (i), (ii) and (iii) are different.

In various embodiments of the present disclosure, the reference CEVal levels at about day 150 to about day 200 of the smoking cessation program (e.g. day 170 to day 190) are:

i. <about 54 to <about 35 pmol/g Hb CEVal for compliance;

ii. between about 35 and about 112 pmol/g Hb CEVal for partial compliance; and iii. >about 90 to >about 112 pmol/g Hb CEVal for non-compliance;

provided that (i), (ii) and (iii) are different.

In various embodiments of the present disclosure, the reference CEVal levels at about day 150 to about day 200 of the smoking cessation program (e.g. day 170 to day 190) are:

i. <about 54 to <about 35 pmol/g Hb CEVal for compliance;

ii. between about 35 and about 112 pmol/g Hb CEVal for partial compliance; and iii. >about 100 to >about 112 pmol/g Hb CEVal for non-compliance;

provided that (i), (ii) and (iii) are different.

In various embodiments of the present disclosure, the reference CEVal levels at about day 150 to about day 200 of the smoking cessation program (e.g. day 170 to day 190) are:

i. <about 54 to <about 35 pmol/g Hb CEVal for compliance;

ii. between about 35 and about 112 pmol/g Hb CEVal for partial compliance; and iii. >about 112 pmol/g Hb CEVal for non-compliance;

provided that (i), (ii) and (iii) are different.

In various embodiments of the present disclosure, the reference CEVal levels at about day 150 to about day 200 of the smoking cessation program (e.g. day 170 to day 190) are:

i. <about 54 to <about 35 pmol/g Hb CEVal for compliance;

ii. between about 40 and about 112 pmol/g Hb CEVal for partial compliance; and iii. >about 70 to >about 112 pmol/g Hb CEVal for non-compliance;

provided that (i), (ii) and (iii) are different.

In various embodiments of the present disclosure, the reference CEVal levels at about day 150 to about day 200 of the smoking cessation program (e.g. day 170 to day 190) are:

i. <about 54 to <about 35 pmol/g Hb CEVal for compliance;
ii. between about 45 and about 112 pmol/g Hb CEVal for partial compliance; and
iii. >about 70 to >about 112 pmol/g Hb CEVal for non-compliance;
provided that (i), (ii) and (iii) are different.

In various embodiments of the present disclosure, the reference CEVal levels at about day 150 to about day 200 of the smoking cessation program (e.g. day 170 to day 190) are:
i. <about 54 to <about 35 pmol/g Hb CEVal for compliance;
ii. between about 50 and about 112 pmol/g Hb CEVal for partial compliance; and
iii. >about 80 to >about 112 pmol/g Hb CEVal for non-compliance;
provided that (i), (ii) and (iii) are different.

In various embodiments of the present disclosure, the reference CEVal levels at about day 150 to about day 200 of the smoking cessation program (e.g. day 170 to day 190) are:
i. <about 54 to <about 35 pmol/g Hb CEVal for compliance;
ii. between about 54 and about 112 pmol/g Hb CEVal for partial compliance; and
iii. >about 90 to >about 112 pmol/g Hb CEVal for non-compliance;
provided that (i), (ii) and (iii) are different.

In various embodiments of the present disclosure, the reference CEVal levels at about day 150 to about day 200 of the smoking cessation program (e.g. day 170 to day 190) are:
i. <about 54 to <about 35 pmol/g Hb CEVal for compliance;
ii. between about 54 and about 112 pmol/g Hb CEVal for partial compliance; and
iii. >about 100 to >about 112 pmol/g Hb CEVal for non-compliance;
provided that (i), (ii) and (iii) are different.

In various embodiments of the present disclosure, the reference CEVal levels at about day 150 to about day 200 of the smoking cessation program (e.g. day 170 to day 190) are:
i. <about 54 to <about 35 pmol/g Hb CEVal for compliance;
ii. between about 54 and about 112 pmol/g Hb CEVal for partial compliance; and
iii. >about 112 pmol/g Hb CEVal for non-compliance;
provided that (i), (ii) and (iii) are different.

In the latter, the "cut-off" for compliance is about 54 pmol/g Hb CEVal and the cut-off for non-compliance is about 112 pmol/g Hb.

In various embodiments of the present disclosure, the reference CEVal levels at about day 150 to about day 200 of the smoking cessation program (e.g. day 170 to day 190) are:
i. <about 45 to <about 25 pmol/g Hb CEVal for compliance;
ii. between about 25 and about 112 pmol/g Hb CEVal for partial compliance; and
iii. >about 45 to >about 112 pmol/g Hb CEVal for non-compliance;
provided that (i), (ii) and (iii) are different.

In various embodiments of the present disclosure, the reference CEVal levels at about day 150 to about day 200 of the smoking cessation program (e.g. day 170 to day 190) are:
i. <about 45 to <about 25 pmol/g Hb CEVal for compliance;
ii. between about 25 and about 100 pmol/g Hb CEVal for partial compliance; and
iii. >about 45 to >about 100 pmol/g Hb CEVal for non-compliance;
provided that (i), (ii) and (iii) are different.

In various embodiments of the present disclosure, the reference CEVal levels at about day 150 to about day 200 of the smoking cessation program (e.g. day 170 to day 190) are:
i. <about 45 to <about 25 pmol/g Hb CEVal for compliance;
ii. between about 25 and about 80 pmol/g Hb CEVal for partial compliance; and
iii. >about 45 to >about 80 pmol/g Hb CEVal for non-compliance; provided that (i), (ii) and (iii) are different.

In various embodiments of the present disclosure, the reference CEVal levels at about day 150 to about day 200 of the smoking cessation program (e.g. day 170 to day 190) are:
i. <about 25 pmol/g Hb CEVal for compliance;
ii. between about 25 and about 80 pmol/g Hb CEVal for partial compliance; and
iii. >about 45 to >about 80 pmol/g Hb CEVal for non-compliance;
provided that (i), (ii) and (iii) are different.

In various embodiments of the present disclosure, the reference CEVal levels at about day 150 to about day 200 of the smoking cessation program (e.g. day 170 to day 190) are:
i. <about 25 pmol/g Hb CEVal for compliance;
ii. between about 25 and about 80 pmol/g Hb CEVal for partial compliance; and
iii. >about 60 pmol/g Hb CEVal for non-compliance;
provided that (i), (ii) and (iii) are different.

In various embodiments of the present disclosure, the reference CEVal levels at about day 150 to about day 200 of the smoking cessation program (e.g. day 170 to day 190) are:
i. <about 25 pmol/g Hb CEVal for compliance;
ii. between about 25 and about 77 pmol/g Hb CEVal for partial compliance; and
iii. >about 77 pmol/g Hb CEVal for non-compliance;
provided that (i), (ii) and (iii) are different.

In various embodiments of the present disclosure, at about day 300 to about day 370 of the smoking cessation program (e.g. day 350 to day 370), i.e. day 300 to day 370 or day 350 to day 370 from T0, the reference CEVal levels are:
i. <about 35 to <about 20 pmol/g Hb CEVal for compliance;
ii. between about 20 and about 78 pmol/g Hb CEVal for partial compliance; and
iii. ≥about 40 to ≥about 78 pmol/g Hb CEVal for non-compliance;
provided that (i), (ii) and (iii) are different.

In various embodiments of the present disclosure, at about day 300 to about day 370 or about day 350 to about day 370 of the smoking cessation program, the reference CEVal levels are:
i. <about 35 to <about 20 pmol/g Hb CEVal for compliance;
ii. between about 25 and about 78 pmol/g Hb CEVal for partial compliance; and
iii. ≥about 40 to ≥about 78 pmol/g Hb CEVal for non-compliance;
provided that (i), (ii) and (iii) are different.

In various embodiments of the present disclosure, at about day 300 to about day 370 or about day 350 to about day 370 of the smoking cessation program, the reference CEVal levels are:
i. <about 35 to <about 20 pmol/g Hb CEVal for compliance;
ii. between about 30 and about 78 pmol/g Hb CEVal for partial compliance; and iii. ≥about 40 to ≥about 78 pmol/g Hb CEVal for non-compliance;

provided that (i), (ii) and (iii) are different.

In various embodiments of the present disclosure, at about day 300 to about day 370 or about day 350 to about day 370 of the smoking cessation program, the reference CEVal levels are:

i. <about 35 to <about 20 pmol/g Hb CEVal for compliance;

ii. between about 35 and about 78 pmol/g Hb CEVal for partial compliance; and iii. ≥about 40 to ≥about 78 pmol/g Hb CEVal for non-compliance;

provided that (i), (ii) and (iii) are different.

In various embodiments of the present disclosure, at about day 300 to about day 370 or about day 350 to about day 370 of the smoking cessation program, the reference CEVal levels are:

i. <about 35 to <about 20 pmol/g Hb CEVal for compliance;

ii. between about 20 and about 78 pmol/g Hb CEVal for partial compliance; and iii. ≥about 45 to ≥about 78 pmol/g Hb CEVal for non-compliance;

provided that (i), (ii) and (iii) are different.

In various embodiments of the present disclosure, at about day 300 to about day 370 or about day 350 to about day 370 of the smoking cessation program, the reference CEVal levels are:

i. <about 35 to <about 20 pmol/g Hb CEVal for compliance;

ii. between about 20 and about 78 pmol/g Hb CEVal for partial compliance; and iii. ≥about 50 to ≥about 78 pmol/g Hb CEVal for non-compliance;

provided that (i), (ii) and (iii) are different.

In various embodiments of the present disclosure, at about day 300 to about day 370 or about day 350 to about day 370 of the smoking cessation program, the reference CEVal levels are:

i. <about 35 to <about 20 pmol/g Hb CEVal for compliance;

ii. between about 20 and about 78 pmol/g Hb CEVal for partial compliance; and iii. ≥about 55 to ≥about 78 pmol/g Hb CEVal for non-compliance;

provided that (i), (ii) and (iii) are different.

In various embodiments of the present disclosure, at about day 300 to about day 370 or about day 350 to about day 370 of the smoking cessation program, the reference CEVal levels are:

i. <about 35 to <about 20 pmol/g Hb CEVal for compliance;

ii. between about 20 and about 78 pmol/g Hb CEVal for partial compliance; and iii. ≥about 60 to ≥about 78 pmol/g Hb CEVal for non-compliance;

provided that (i), (ii) and (iii) are different.

In various embodiments of the present disclosure, at about day 300 to about day 370 or about day 350 to about day 370 of the smoking cessation program, the reference CEVal levels are:

i. <about 35 to <about 20 pmol/g Hb CEVal for compliance;

ii. between about 20 and about 78 pmol/g Hb CEVal for partial compliance; and iii. ≥about 65 to ≥about 78 pmol/g Hb CEVal for non-compliance;

provided that (i), (ii) and (iii) are different.

In various embodiments of the present disclosure, at about day 300 to about day 370 or about day 350 to about day 370 of the smoking cessation program, the reference CEVal levels are:

i. <about 35 to <about 20 pmol/g Hb CEVal for compliance;

ii. between about 20 and about 78 pmol/g Hb CEVal for partial compliance; and iii. ≥about 70 to ≥about 78 pmol/g Hb CEVal for non-compliance;

provided that (i), (ii) and (iii) are different.

In various embodiments of the present disclosure, at about day 300 to about day 370 or about day 350 to about day 370 of the smoking cessation program, the reference CEVal levels are:

i. <about 35 to <about 20 pmol/g Hb CEVal for compliance;

ii. between about 20 and about 78 pmol/g Hb CEVal for partial compliance; and iii. ≥about 78 pmol/g Hb CEVal for non-compliance;

provided that (i), (ii) and (iii) are different.

In various embodiments of the present disclosure, at about day 300 to about day 370 or about day 350 to about day 370 of the smoking cessation program, the reference CEVal levels are:

i. <about 35 to <about 20 pmol/g Hb CEVal for compliance;

ii. between about 25 and about 78 pmol/g Hb CEVal for partial compliance; and iii. ≥about 45 to ≥about 78 pmol/g Hb CEVal for non-compliance;

provided that (i), (ii) and (iii) are different.

In various embodiments of the present disclosure, at about day 300 to about day 370 or about day 350 to about day 370 of the smoking cessation program, the reference CEVal levels are:

i. <about 35 to <about 20 pmol/g Hb CEVal for compliance;

ii. between about 30 and about 78 pmol/g Hb CEVal for partial compliance; and iii. ≥about 50 to ≥about 78 pmol/g Hb CEVal for non-compliance;

provided that (i), (ii) and (iii) are different.

In various embodiments of the present disclosure, at about day 300 to about day 370 or about day 350 to about day 370 of the smoking cessation program, the reference CEVal levels are:

i. <about 35 to <about 20 pmol/g Hb CEVal for compliance;

ii. between about 35 and about 78 pmol/g Hb CEVal for partial compliance; and iii. ≥about 50 to ≥about 78 pmol/g Hb CEVal for non-compliance;

provided that (i), (ii) and (iii) are different.

In various embodiments of the present disclosure, at about day 300 to about day 370 or about day 350 to about day 370 of the smoking cessation program, the reference CEVal levels are:

i. <about 35 to <about 20 pmol/g Hb CEVal for compliance;

ii. between about 35 and about 78 pmol/g Hb CEVal for partial compliance; and iii. ≥about 55 to ≥about 78 pmol/g Hb CEVal for non-compliance;

provided that (i), (ii) and (iii) are different.

In various embodiments of the present disclosure, at about day 300 to about day 370 or about day 350 to about day 370 of the smoking cessation program, the reference CEVal levels are:

i. <about 35 to <about 20 pmol/g Hb CEVal for compliance;

ii. between about 35 and about 78 pmol/g Hb CEVal for partial compliance; and iii. ≥about 60 to ≥about 78 pmol/g Hb CEVal for non-compliance;

provided that (i), (ii) and (iii) are different.

In various embodiments of the present disclosure, at about day 300 to about day 370 or about day 350 to about day 370 of the smoking cessation program, the reference CEVal levels are:

i. <about 35 to <about 20 pmol/g Hb CEVal for compliance;

ii. between about 35 and about 78 pmol/g Hb CEVal for partial compliance; and iii. ≥about 65 to ≥about 78 pmol/g Hb CEVal for non-compliance;

provided that (i), (ii) and (iii) are different.

In various embodiments of the present disclosure, at about day 300 to about day 370 or about day 350 to about day 370 of the smoking cessation program, the reference CEVal levels are:

i. <about 35 to <about 20 pmol/g Hb CEVal for compliance;

ii. between about 35 and about 78 pmol/g Hb CEVal for partial compliance; and iii. ≥about 70 to ≥about 78 pmol/g Hb CEVal for non-compliance;

provided that (i), (ii) and (iii) are different.

In various embodiments of the present disclosure, at about day 300 to about day 370 or about day 350 to about day 370 of the smoking cessation program, the reference CEVal levels are:

i. <about 35 to <about 20 pmol/g Hb CEVal for compliance;

ii. between about 35 and about 78 pmol/g Hb CEVal for partial compliance; and iii. ≥about 78 pmol/g Hb CEVal for non-compliance;

provided that (i), (ii) and (iii) are different.

In various embodiments of the present disclosure, at about day 300 to about day 370 or about day 350 to about day 370 of the smoking cessation program, the reference CEVal levels are:

i. <about 35 pmol/g Hb CEVal for compliance;

ii. between about 35 and about 78 pmol/g Hb CEVal for partial compliance; and iii. ≥about 78 pmol/g Hb CEVal for non-compliance;

provided that (i), (ii) and (iii) are different.

In various embodiments of the present disclosure, at about day 300 to about day 370 or about day 350 to about day 370 of the smoking cessation program, the reference CEVal levels are:

i. <about 35 to <about 10 pmol/g Hb CEVal for compliance;

ii. between about 10 and about 78 pmol/g Hb CEVal for partial compliance; and iii. >about 20 to >about 78 pmol/g Hb CEVal for non-compliance;

provided that (i), (ii) and (iii) are different.

In various embodiments of the present disclosure, at about day 300 to about day 370 or about day 350 to about day 370 of the smoking cessation program, the reference CEVal levels are:

i. <about 25 to <about 10 pmol/g Hb CEVal for compliance;

ii. between about 10 and about 50 pmol/g Hb CEVal for partial compliance; and iii. >about 20 to >about 40 pmol/g Hb CEVal for non-compliance;

provided that (i), (ii) and (iii) are different.

In various embodiments of the present disclosure, at about day 300 to about day 370 or about day 350 to about day 370 of the smoking cessation program, the reference CEVal levels are:

i. <about 25 to <about 10 pmol/g Hb CEVal for compliance;

ii. between about 10 and about 40 pmol/g Hb CEVal for partial compliance; and iii. >about 20 pmol/g Hb CEVal for non-compliance;

provided that (i), (ii) and (iii) are different.

In various embodiments of the present disclosure, at about day 300 to about day 370 or about day 350 to about day 370 of the smoking cessation program, the reference CEVal levels are:

i. <about 10 pmol/g Hb CEVal for compliance;

ii. between about 10 and about 40 pmol/g Hb CEVal for partial compliance; and iii. >about 20 pmol/g Hb CEVal for non-compliance;

provided that (i), (ii) and (iii) are different.

In various embodiments of the present disclosure, at about day 300 to about day 370 or about day 350 to about day 370 of the smoking cessation program, the reference CEVal levels are:

i. <about 10 pmol/g Hb CEVal for compliance;

ii. between about 10 and about 25 pmol/g Hb CEVal for partial compliance; and iii. >about 20 pmol/g Hb CEVal for non-compliance;

provided that (i), (ii) and (iii) are different.

In various embodiments of the present disclosure, at about day 300 to about day 370 or about day 350 to about day 370 of the smoking cessation program, the reference CEVal levels are:

i. <about 10 pmol/g Hb CEVal for compliance;

ii. between about 10 and about 22 pmol/g Hb CEVal for partial compliance; and iii. >about 22 pmol/g Hb CEVal for non-compliance;

provided that (i), (ii) and (iii) are different.

These reference CEVal levels (in pmol/g Hb) and time periods are summarized in the table below:

| | Day 80 to Day 100 | Day 170 to Day 190 | Day 350 to Day 370 | Estimated Cigarettes per week |
|---|---|---|---|---|
| Compliant | <78 to <40 | <54 to <35 | <35 to <20 | up to 4 |
| Partially compliant | 60-78 to 164 | 35-54 to 112 | 20-35 to 78 | >4 to 10 |
| Non-compliant | >78 to >164 | >60 to >112 | >40 to >78 | >10 |

In various embodiments of the present disclosure, the reference CEVal reference levels (in pmol/g Hb) and time periods are:

| | Day 80 to Day 100 | Day 170 to Day 190 | Day 350 to Day 370 | Estimated Cigarettes per week |
|---|---|---|---|---|
| Compliant | <78 | <54 | <35 | up to 4 |
| Partially compliant | 78 to 164 | 54 to 112 | 35 to 78 | >4 to 10 |
| Non-compliant | >164 | >112 | >78 | >10 |

In various embodiments of the present disclosure, the reference CEVal levels (in pmol/g Hb) and time periods:

| | Day 80 to Day 100 | Day 170 to Day 190 | Day 350 to Day 370 | Estimated Cigarettes per week |
|---|---|---|---|---|
| Compliant | <78 to <40 | <45 to <25 | <35 to <10 | up to 4 |
| Partially compliant | 60-76 to 150 | 25 to 112 | 10 to 78 | >4 to 10 |
| Non-compliant | >142 to >150 | >45 to >112 | >20 to >78 | >10 |

In various embodiments of the present disclosure, the reference CEVal levels (in pmol/g Hb) and time periods are:

| | Day 80 to Day 100 | Day 170 to Day 190 | Day 350 to Day 370 | Estimated Cigarettes per week |
|---|---|---|---|---|
| Compliant | <76 | <25 | <10 | up to 4 |
| Partially compliant | 76 to 142 | 25 to 77 | 10 to 22 | >4 to 10 |
| Non-compliant | >142 | >77 | >22 | >10 |

Other embodiments are presented above.

Method of Assessing Compliance

The above-described smoking cessation program(s), measurement method(s) and reference levels (cut-off values) of CEVal are applicable to both the use of the first aspect described herein, and the method of assessing compliance of the second aspect. The method comprises steps (a) to (d), in order. Step (a) involves providing one or more blood samples from a subject. The blood sample may be whole blood.

The method of obtaining the sample is not part of the present disclosure. The sample may be provided by any method known in the art, and once provided, the sample is subjected to step (b) where the level of CEVal is measured in a biological assay as described above. This level obtained in step (b) is then compared in step (c) with reference levels of CEVal for the smoking cessation program, and the subject is stratified in step (d) according to compliance with the smoking cessation program based on the comparison in step (c).

To assess a subjects' continued compliance, the provision of a sample, assaying, comparing and stratifying steps, i.e., steps (a) to (d) of the method described herein, can be run repeatedly during the course of the smoking cessation program. In various embodiments of the present disclosure, steps (a) to (d) are carried out at pre-determined time intervals from the start of the smoking cessation program. For example, from T0 (the start of the smoking cessation program) steps (a) to (d) may be carried out every month, every two months, every three months, every six months, every year or a combination thereof. In various embodiments of the present disclosure, steps (a) to (d) may be carried out after about a month (e.g., about 30 days) from T0, after about three months (e.g., about 90 days such as 80 to 100 days), after about six months (e.g., about 180 days such as 170 to 190 days), after about twelve months (e.g. about 360 days, such as 350 to 370 days) or a combination thereof.

In various embodiments of the present disclosure, steps (a) to (d) are carried out after at least about three months (e.g., about 80 to 100 such as 90 days) from T0. Additionally, steps (a) to (d) may be carried out after at least about six months (e.g., about 170 to 190, such as 180 days) from T0. For long-term studies, steps (a) to (d) may further be carried out after about twelve months (e.g., about 350 to 370, such as 360 days) from T0.

In various embodiments of the present disclosure, the reference CEVal levels are associated with the time interval at which steps (a) to (d) are conducted. The stratification may therefore involve CEVal reference or cut-off values for compliance or non-compliance as defined above, or for compliance, partial compliance or non-compliance as defined above.

In various embodiments of the present disclosure, the method may further comprise a step (e) of modifying or maintaining the smoking cessation program for the subject based on the stratification in step (d). The nature of the modification is not limited and can be any modification known in the art. The modification may, for example, involve nicotine replacement, lifestyle choices or other therapy to help the subject with their compliance to the smoking cessation program. Such other therapy can include drug therapy such as drug prescription therapy, nutritional therapy, psychological counselling, advice on lifestyle choices, or a combination thereof. Examples of nicotine replacement therapy may include sprays, inhalers, gums, lozenges and transdermal nicotine-delivery patches. Lifestyle choices may involve changes in diet and nutrition, changes in exercise, smoking elimination or a combination thereof.

The modification may include positive or negative reinforcement to motivate the subject's compliance.

The invention will now be described with reference to the following non-limiting examples.

EXAMPLES

Example 1

To verify the reference CEVal level at a nominal 90 days (±5 days) of a smoking cessation program, 197 subjects were enrolled in a smoking cessation program where they were asked to replace their smoking of conventional cigarettes with a commercially available tobacco heating product: Glo™ from British American Tobacco. Subjects were chosen on the basis that they did not intend to quit smoking. Alongside these subjects, 190 subjects were enrolled in a smoking cessation program where they were given access to psychological counselling and nicotine replacement therapy. The latter subjects were chosen on the basis that they have a high intent to quit smoking. 40 never smokers were used as a control group.

The 197 subjects (smokers) that were asked to replace conventional cigarettes with the tobacco heating product (THP) were further split into subjects who would continue smoking cigarettes for the duration of the program, and subjects who would completely switch to THP. The subject groups were therefore:

A: Smokers provided with THP who would continue smoking cigarettes.

B: Smokers provided with THP who would not continue smoking cigarettes.

C: Smokers provided with counselling and nicotine replacement therapy intending to cease all smoking.

D: Never smokers, defined as having smoked <100 cigarettes in their lifetime and none in the 30 day before the start of the smoking cessation program.

Each subject was provided with the necessary materials for their cessation program, e.g. tobacco heating product, nicotine replacement or access to counselling, at the start of the smoking cessation program (T0), and sent away to resume their normal lifestyle and habits. After 90 days from T0, the subjects returned to the smoking cessation program center for various tests and health-checks to be run. These tests and health-checks included the taking of a blood sample from each subject.

Each blood sample was tested according to the method set out in Scherer et al., Biomarkers, 2014 June; 19(4): 291-301, and a CEVal level determined.

The CEVal levels determined for each subject group were then compared to the following reference CEVal levels in order to stratify subjects in all groups according to compliance with the respective smoking cessation program:

| Level of Compliance | CEVal level (pmol/g Hb) |
|---|---|
| Compliant | <78 |
| Partially compliant (Dual Use) | 78 to 164 |
| Non-compliant | >164 |

The data for the subjects in groups C and D confirmed the reference CEVal level for compliance. Along with the data for the subjects in groups A and B, the reference CEVal levels for partial compliance and non-compliance were also verified.

Example 2

To verify the reference CEVal level at a nominal 180 days (±14 days) of a smoking cessation program, the subjects of Example 1 continued their smoking cessation program and returned to the smoking cessation program center after 180 days from T0 for further tests and health-checks. A blood sample was taken from each subject and tested according to the method set out in Scherer et al., Biomarkers, 2014 June; 19(4): 291-301 to determine a CEVal level. This CEVal level was then compared to the following reference CEVal levels in order to stratify subjects according to compliance with the respective smoking cessation program:

| Level of Compliance | CEVal level (pmol/g Hb) |
|---|---|
| Compliant | <54 |
| Partially compliant (Dual Use) | 54 to 112 |
| Non-compliant | >112 |

The CEVal level was alternatively compared to the following reference levels in order to stratify subjects according to compliance with the respective smoking cessation program:

| Level of Compliance | CEVal level (pmol/g Hb) |
|---|---|
| Compliant | <25 |
| Partially compliant (Dual Use) | 25 to 77 |
| Non-compliant | >77 |

Example 3

To verify the reference CEVal level at a nominal 360 days (±14 days) of a smoking cessation program, the subjects of Examples 1 and 2 continued their smoking cessation program and returned to the smoking cessation program center after 360 days from T0 for further tests and health-checks. A blood sample was taken from each subject and tested according to the method set out in Scherer et al., Biomarkers, 2014 June; 19(4): 291-301 to determine a CEVal level. This CEVal level was then compared to the following reference CEVal levels in order to stratify subjects according to compliance with the respective smoking cessation program:

| Level of Compliance | CEVal level (pmol/g Hb) |
|---|---|
| Compliant | <10 |
| Partially compliant (Dual Use) | 10 to 22 |
| Non-compliant | >22 |

The various embodiments described herein are presented only to assist in understanding and teaching the claimed features. These embodiments are provided as a representative sample of embodiments only, and are not exhaustive and/or exclusive. It is to be understood that advantages, embodiments, examples, functions, features, structures, and/or other aspects described herein are not to be considered limitations on the scope of the disclosure as defined by the claims or limitations on equivalents to the claims, and that other embodiments may be utilized and modifications may be made without departing from the scope of the claimed disclosure. Various embodiments of the present disclosure may suitably comprise, consist of, or consist essentially of, appropriate combinations of the disclosed elements, components, features, parts, steps, means etc. other than those specifically described herein. In addition, this disclosure may include other disclosures not presently claimed, but which may be claimed in future.

The invention claimed is:

1. A method of assessing compliance with a smoking cessation program, said method comprising:

(a) providing one or more blood samples from a subject;

(b) measuring the level of N-(2-cyanoethyl) valine (CEVal) from the one or more blood samples of the subject in a biological assay;

(c) comparing the level obtained in step (b) with reference levels of CEVal for the smoking cessation program; and (d) stratifying the subject according to compliance with the smoking cessation program based on the comparison in step (c); and (e) modifying or maintaining the smoking cessation program for the subject based on the stratification in step (d);

wherein the smoking cessation program comprises switching from combustible smoking articles to a non-combustible aerosol provision system, nicotine replacement therapy, lifestyle choices, therapy or a combination thereof;

wherein the reference levels of CEVal are indicative of compliance or non-compliance with the smoking cessation program, or indicative of compliance, partial compliance or non-compliance with the smoking cessation program;

wherein the smoking cessation program has a length of at least 80 days and wherein the reference CEVal levels at about day 80 to about day 100 of the smoking cessation program are:

i. <about 78 to <about 40 pmol/g Hb CEVal for compliance; and ii. ≥60 to ≥about 78 pmol/g Hb CEVal for non-compliance;

provided that (i) and (ii) are different; or i. <about 78 to <about 40 pmol/g Hb CEVal for compliance;

ii. between about 60 and about 164 pmol/g Hb CEVal for partial compliance; and iii. >about 78 to >about 164 pmol/g Hb CEVal for non-compliance;

provided that (i), (ii) and (iii) are different.

2. The method of claim 1, wherein steps (a), (b), (c) and (d) are carried out repeatedly during the course of the smoking cessation program to assess the subject's continued compliance.

3. The method of claim 1, wherein the reference CEVal levels at about day 170 to about day 190 of the smoking cessation program are:

i. <about 54 to <about 35 pmol/g Hb CEVal for compliance; and ii. ≥about 35 to ≥about 54 pmol/g Hb CEVal or greater for non-compliance, provided that (i) and (ii) are different; or i. <about 54 to <about 35 pmol/g Hb CEVal for compliance;

ii. between about 35 and about 112 pmol/g Hb CEVal for partial compliance; and iii. >about 60 to >about 112 pmol/g Hb CEVal for non-compliance;

provided that (i), (ii) and (iii) are different.

4. The method of claim 1, wherein the reference CEVal levels at about day 350 to about day 370 of the smoking cessation program are:

i. <about 35 to <about 20 pmol/g Hb CEVal for compliance; and ii. ≥about 20 to ≥about 35 pmol/g Hb CEVal for non-compliance provided that (i) and (ii) are different;

or i. <about 35 to <about 20 pmol/g Hb CEVal for compliance;

ii. between about 20 and about 78 pmol/g Hb CEVal for partial compliance; and iii. >about 40 to >about 78 pmol/g Hb CEVal for non-compliance;

provided that (i), (ii) and (iii) are different.

5. A method of assessing compliance with a smoking cessation program, said method comprising:

(a) providing one or more blood samples from a subject;

(b) measuring the level of N-(2-cyanoethyl) valine (CEVal) from the one or more blood samples of the subject in a biological assay;

(c) comparing the level obtained in step (b) with reference levels of CEVal for the smoking cessation program;

(d) stratifying the subject according to compliance with the smoking cessation program based on the comparison in step (c); and (e) modifying or maintaining the smoking cessation program for the subject based on the stratification in step (d);

wherein the smoking cessation program comprises switching from combustible smoking articles to a non-combustible aerosol provision system, nicotine replacement therapy, lifestyle choices, therapy or a combination thereof;

wherein the reference levels of CEVal are indicative of compliance or non-compliance with the smoking cessation program, or indicative of compliance, partial compliance or non-compliance with the smoking cessation program;

wherein the smoking cessation program has a length of at least 80 days and wherein the reference CEVal levels at about day 80 to about day 100 of the smoking cessation program are:

i. <about 78 to <about 40 pmol/g Hb CEVal for compliance;

ii. between about 60 and about 150 pmol/g Hb CEVal for partial compliance; and iii. >about 78 to >about 150 pmol/g Hb CEVal for non-compliance;

provided that (i), (ii) and (iii) are different.

6. The method of claim 5, wherein the reference levels are:

i. <about 76 pmol/g Hb CEVal for compliance;

ii. between about 76 and about 142 pmol/g Hb CEVal for partial compliance; and iii. >about 142 pmol/g Hb CEVal for non-compliance;

provided that (i), (ii) and (iii) are different.

7. The method of claim 5, wherein the reference CEVal levels at about day 170 to about day 190 of the smoking cessation program are:

i. <about 45 to <about 25 pmol/g Hb CEVal for compliance;

ii. between about 25 and about 100 pmol/g Hb CEVal for partial compliance; and iii. >about 45 to >about 100 pmol/g Hb CEVal for non-compliance;

provided that (i), (ii) and (iii) are different.

8. The method of claim 7, wherein the reference levels are:

i. <about 25 pmol/g Hb CEVal for compliance;

ii. between about 25 and about 77 pmol/g Hb CEVal for partial compliance; and iii. >about 77 pmol/g Hb CEVal for non-compliance;

provided that (i), (ii) and (iii) are different.

9. The method of claim 5, wherein the reference CEVal levels at about day 350 to about day 370 of the smoking cessation program are:

i. <about 25 to <about 10 pmol/g Hb CEVal for compliance;

ii. between about 10 and about 40 pmol/g Hb CEVal for partial compliance; and iii. >about 20 pmol/g Hb CEVal for non-compliance, provided that (i), (ii) and (iii) are different.

10. The method of claim 9, wherein the reference levels are:

i. <about 10 pmol/g Hb CEVal for compliance;

ii. between about 10 and about 22 pmol/g Hb CEVal for partial compliance; and iii. >about 22 pmol/g Hb CEVal for non-compliance, provided that (i), (ii) and (iii) are different.

* * * * *